(12) United States Patent
Wang et al.

(10) Patent No.: US 11,906,503 B2
(45) Date of Patent: Feb. 20, 2024

(54) ISOTOPOCULE ANALYSIS OF HYDROCARBON CONTAMINATION

(71) Applicant: ExxonMobil Technology and Engineering Company, Spring, TX (US)

(72) Inventors: David T. Wang, Witchita Falls, TX (US); Muhammad Asif, The Woodlands, TX (US); Michael J. Formolo, The Woodlands, TX (US)

(73) Assignee: ExxonMobil Technology and Engineering Company, Spring, TX (US)

( * ) Notice: Subject to any disclaimer, the term of this patent is extended or adjusted under 35 U.S.C. 154(b) by 198 days.

(21) Appl. No.: 17/304,974

(22) Filed: Jun. 29, 2021

(65) Prior Publication Data
US 2022/0003740 A1 Jan. 6, 2022

Related U.S. Application Data

(60) Provisional application No. 62/705,529, filed on Jul. 2, 2020.

(51) Int. Cl.
*G01N 33/28* (2006.01)
*G01N 21/39* (2006.01)
(Continued)

(52) U.S. Cl.
CPC ......... *G01N 33/2835* (2013.01); *B01D 15/08* (2013.01); *G01N 21/39* (2013.01); *G01N 27/62* (2013.01)

(58) Field of Classification Search
CPC .... B01D 15/08; G01N 33/2835; G01N 21/39; G01N 27/62
See application file for complete search history.

(56) References Cited

U.S. PATENT DOCUMENTS 9,146,225 B2 * 9/2015 Pottorf .................... G01V 9/005
11,237,147 B2 * 2/2022 Peterson ................. E21B 47/11
(Continued)

FOREIGN PATENT DOCUMENTS

CA      2951281 C    *   1/2019            B63B 22/24
CN    105921136 A   *   9/2016            B01D 15/08

OTHER PUBLICATIONS

English translation of Qi, CN105921136 accessed from iq.ip.com Mar. 7, 2023.*

(Continued)

*Primary Examiner* — Kristina M Deherrera
*Assistant Examiner* — Jean F Morello
(74) *Attorney, Agent, or Firm* — Lempia Summerfield Katz LLC

(57) ABSTRACT

Methods for identifying hydrocarbon contamination sources may include fingerprinting hydrocarbons using isotopocule analyses for BTEX compounds. For example, methods for identifying hydrocarbon contamination sources may comprise: extracting BTEX compounds from a sample; measuring the isotopocule composition of the BTEX compounds; and determining a characteristic of the sample based on the isotopocule composition. Such characteristics may include, but are not limited to, the characteristic of the sample comprises one or more selected from the group consisting of: a source of the sample, a condition at which the sample formed or was last equilibrated, a migration time from a source to a sample location, weathering of the sample, and degree to which the sample is anthropogenic and naturally-occurring.

22 Claims, 1 Drawing Sheet

(51) Int. Cl.
  *B01D 15/08*   (2006.01)
  *G01N 27/62*   (2021.01)

(56) References Cited

U.S. PATENT DOCUMENTS

| | | | | |
|---|---|---|---|---|
| 2004/0164237 A1* | 8/2004 | Jones | ............... | G01N 21/31 |
| | | | | 250/269.1 |
| 2014/0250999 A1* | 9/2014 | Lawson | ............. | E21B 49/02 |
| | | | | 73/152.23 |
| 2018/0245464 A1* | 8/2018 | Formolo | ............. | E21B 49/08 |

OTHER PUBLICATIONS

Cesar, J., et al. (2019) "Isotope heterogeneity in ethyltoluenes from Australian condensates, and their stable carbon site-specific isotope analysis", Organic Geochemistry, vol. 135, pp. 32-37.

Tyler B. Coplen (2011) "Guidelines and recommended terms for expression of stable-isotope-ratio and gas-ratio measurement results", Rapid Communications in Mass Spectrometry, vol. 25, Issue 17, pp. 2538-2560.

John M. Eiler (2013) "The Isotopic Anatomies of Molecules and Minerals", Annu. Rev. Earth Planet Sci., vol. 41, pp. 411-441.

Eiler, J., et al. (2017) "Analysis of molecular isotopic structures at high precision and accuracy by Orbitrap mass spectrometry", International Journal of Mass Spectrometry, vol. 422, pp. 126-142.

Eglinton, T., et al. (1996) "Gas Chromatographic Isolation of Individual Compounds from Complex Matrices for Radiocarbon Dating", Anal. Chem., vol. 68, pp. 904-912.

Saunders, P.C., et al. (1970) "Catalytic Sites for Deuterium Exchange with Benzene over Alumina", The Journal of Physical Chemistry, vol. 74, Issue 25, pp. 4323-4329.

Reddy, C.M., et al. (2012) "Composition and fate of gas and oil released to the water colummn during the Deepwater Horizon oil spill", Proceedings of the National Academy of Sciences, vol. 109, No. 50, pp. 20229-20234.

Tang, C. et al. (2019) "Observation of inconsistent carbon isotope compositions of chlorine-isotopologue pairs of individual organochlorines by gas chromatography-high resolution mass spectrometry", arXiv preprint, arXiv:1907.08897, pp. 1-27.

* cited by examiner

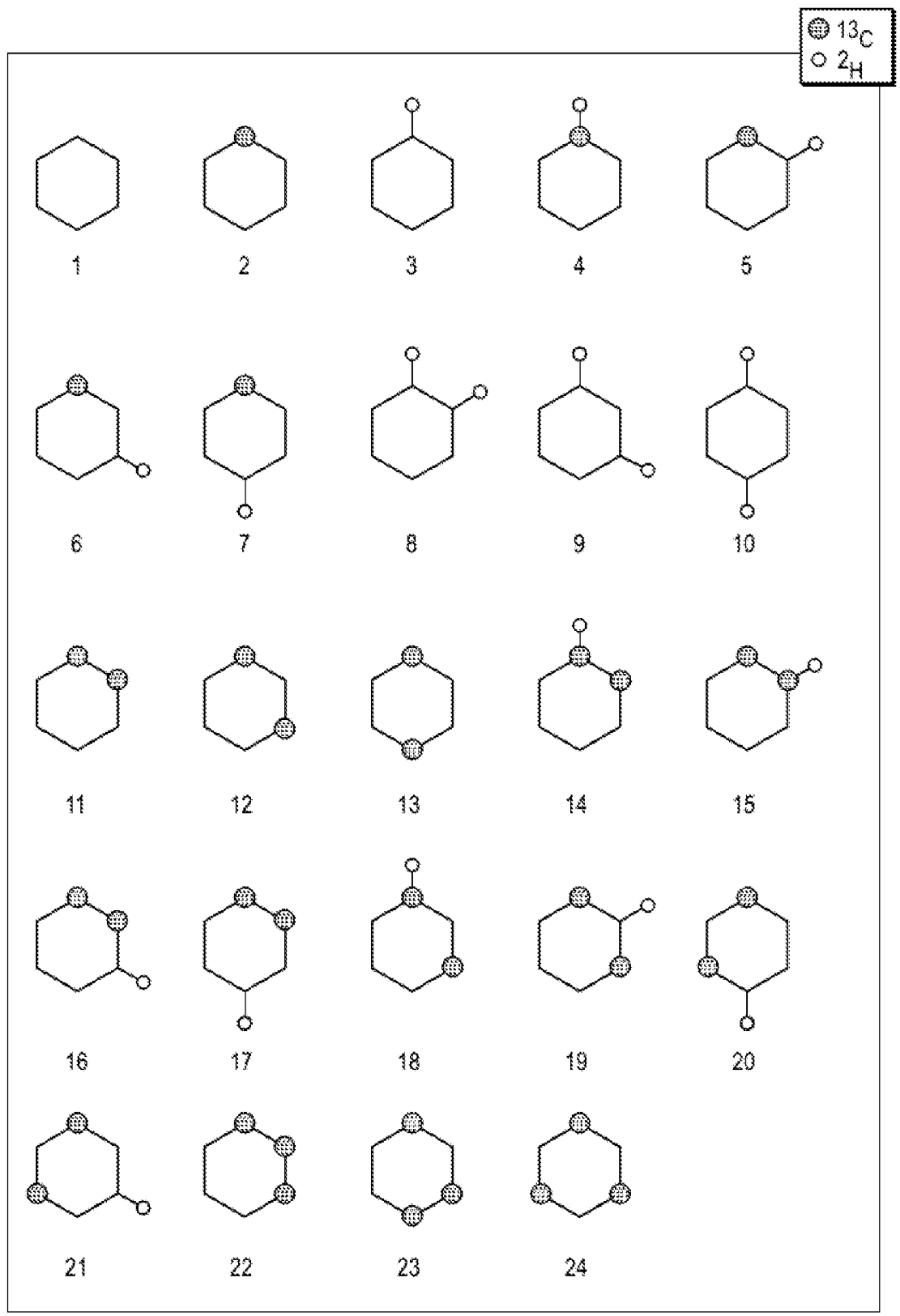

ISOTOPOCULE ANALYSIS OF HYDROCARBON CONTAMINATION

CROSS-REFERENCE TO RELATED APPLICATIONS

This application claims the benefit of U.S. Provisional Application No. 62/705,529, filed Jul. 2, 2020, the entirety of which is incorporated by reference herein.

FIELD OF INVENTION

The present disclosure relates to identifying hydrocarbon contamination sources.

BACKGROUND

Hydrocarbon contaminants found in the environment can be from (a) larger, bolus-like events such as oil spills and wellbore blowouts and (b) smaller, prolonged events such as naturally occurring seeps from hydrocarbon reservoirs, discharges from marine transportation vessels, and leaks in pipelines and storage containers. Ascertaining the source of the hydrocarbon contaminants is important to stopping the contamination and identifying the responsible party (if any).

For a larger event, the source is initially easy to identify. However, because the event is larger, the full impact and scope of the hydrocarbon contamination can be difficult to identify because so much hydrocarbon is released. For example, a wellbore blowout at the ocean floor could take a long time to stop. Where all of the hydrocarbons end up is difficult to identify because of the sheer magnitude of hydrocarbons and the time that has passed.

For a smaller, prolonged event, the source may not be easily identifiable because the hydrocarbon contamination may travel some distance from the source before being observed.

To further complicate identifying the source of hydrocarbon contamination, the hydrocarbon contamination may have multiple sources. Additionally, hydrocarbons in the environment can change over time, which is known as weathering, for example, because of evaporation, dissolution, microbial degradation, photo-oxidation, and interaction between oil and sediments.

Hydrocarbon fingerprinting analysis is used to attempt to identify the source of the hydrocarbon contamination. Techniques for hydrocarbon fingerprinting include chromatography and/or spectroscopy methods to identify (a) the distribution and/or ratio of specific hydrocarbons (e.g., n-alkanes, polycyclic aromatic hydrocarbons, and the like), (b) the ratio of carbon isotopes, and/or (c) the absence/presence of markers (e.g., biomarkers). The hydrocarbon fingerprint analyses are compared to a library of hydrocarbon fingerprints for known sources. However, particularly complex hydrocarbon samples may include multiple source and/or extensive weathering.

SUMMARY OF INVENTION

The present disclosure relates to identifying hydrocarbon contamination sources. More specifically, the present disclosure relates to fingerprinting hydrocarbons using isotopocule analyses for BTEX compounds.

The present disclosure includes a method comprising: extracting BTEX compounds from a sample; measuring the isotopocule composition of the BTEX compounds; and determining a characteristic of the sample based on the isotopocule composition.

The present disclosure also includes a method comprising: extracting BTEX compounds according to Compound 1 from a sample

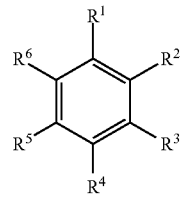

Compound 1 where $R^1$-$R^6$ are independently hydrogen, methyl, ethyl, n-propyl, iso-propyl, hydroxyl, carboxyl, acyl, amino, nitro, sulfo, fluoro, chloro, bromo, or iodo; measuring the isotopocule composition of the BTEX compounds; and determining a characteristic of the sample based on the isotopocule composition, wherein the characteristic of the sample comprises one or more selected from the group consisting of: a source of the sample, a condition at which the sample formed or was last equilibrated, a migration time from a source to a sample location, weathering of the sample, and degree to which the sample is anthropogenic and naturally-occurring.

BRIEF DESCRIPTION OF THE DRAWINGS

The following figures are included to illustrate certain aspects of the disclosure, and should not be viewed as exclusive configurations. The subject matter disclosed is capable of considerable modifications, alterations, combinations, and equivalents in form and function, as will occur to those skilled in the art and having the benefit of this disclosure.

FIG. 1 illustrates 24 isotopocules of benzene where the filled circles are $^{13}C$ and the open circles are $^2H$.

DETAILED DESCRIPTION

The present disclosure relates to identifying hydrocarbon contamination sources. More specifically, the present disclosure relates to fingerprinting hydrocarbons using isotopocule analyses for BTEX compounds.

As used herein, the term "BTEX compounds" refers to one or more of benzene, toluene, ethylbenzene, ortho-xylene, meta-xylene, para-xylene, and other simple benzene derivatives.

As used herein, the term "simple benzene derivatives" refers to derivatives of benzene according to Compound 1, where $R^1$-$R^6$ may independently be hydrogen, methyl, ethyl, n-propyl, iso-propyl, hydroxyl, carboxyl, acyl (encompassing aldehydes, amides, esters, and ketones), amino, nitro, sulfo, fluoro, chloro, bromo, and/or iodo.

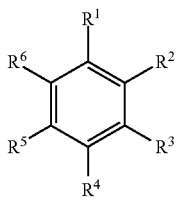

Compound 1

Examples of simple benzene derivatives include, but are not limited to, ethylbenzene, methylethylbenzene, trimethylbenzene, hydroxybenzene (phenol), ortho-dihydroxybenzene, meta-dihydroxybenzene, para-dihydroxybenzene, benzoic acid, benzaldehyde, aniline, benzamide, fluorobenzene, chlorobenzene, ortho-dichlorobenzene, meta-dichlorobenzene, para-dichlorobenzene, bromobenzene, ortho-dibromobenzene, meta-dibromobenzene, para-dibromobenzene, and the like.

As used herein, the term "isotopocules" refers to isotopically-substituted molecules and encompasses isotopomers and isotopologues. As used herein, the term "isotopocule composition" refers to the relative abundance of isotopocules. FIG. 1 illustrates 24 isotopocules of benzene where the filled circles are $^{13}C$ and the open circles are $^{2}H$.

As used herein, the term "isotopomers" refers to isotopic isomers, which differ in the position of the isotopes in the chemical structure.

As used herein, the term "isotopologues" refers to molecules that have the same chemical structure but differ only in their isotopic content.

BTEX compounds are, in general, more volatile, more water-soluble, and more susceptible to weathering than other hydrocarbons. Forensic analysis of hydrocarbon spillage typically does not rely on analyses of BTEX compounds due to their susceptibility to alteration and migration. However, because BTEX compounds are classified by many jurisdictions as priority pollutants, tracking the transport and fate of BTEX compounds in the environment is important to determining a source and liability, if any.

Generally, the methods described herein relate to extracting BTEX compounds from a sample (e.g., a sample having hydrocarbon contamination), measuring the isotopocule composition of the BTEX compounds; and determining a characteristic of the sample (e.g., a source of the sample, a weathering of the sample, and the like) based, at least in part, on the isotopocule composition.

Isotopocule analysis is performed primarily by high-resolution mass spectrometry but other spectroscopic methods are being developed such as high-precision/resolution optical spectroscopy (for example, tunable laser infrared spectroscopy), nuclear magnetic resonance, and wet-chemical decomposition methods (for example, pyrolysis coupled to gas chromatography-isotope ratio mass spectrometry). An isotopocule analysis provides a relative abundance of the different isotopocules in a sample. The abundance and location of carbon isotopes $^{13}C$ in a single compound do not change unless the compound undergoes a chemical reaction that fundamentally alters the ring structure of the BTEX compound (e.g., breaking and reforming C-C bonds by exposure to high temperatures (e.g., greater than about 200° C.) in the presence of a catalyst). Further, the abundance and location of hydrogen isotopes $^{2}H$ is minimally changed by weathering unless a functionalization of the ring structure involves where the $^{2}H$ is located. Further, hydrocarbon samples from different sources and/or having been exposed to different refining techniques have different isotopocule compositions. Therefore, the isotopocule composition of a hydrocarbon contamination should change very little from the source to the location in which the hydrocarbon contamination is observed and/or collected. Therefore, isotopocule analysis methods of BTEX compounds in hydrocarbon contamination samples should more precisely identify the source of the hydrocarbon contamination and other characteristics thereof.

The methods described herein comprise: extracting BTEX compounds from a sample, measuring the isotopocule composition of the BTEX compounds; and determining a characteristic of the sample based, at least in part, on the isotopocule composition.

The sample may comprise water, petroleum, petrochemicals, and/or solid material (e.g., soil or sediment). As used herein, "petroleum" refers to any hydrocarbon phase (e.g., oil, gas, and condensate) formed by natural geological processes. As used herein, the term "petrochemicals" refers to any petroleum-derived chemicals (e.g., fuels, lubricants, polymers, and their constituent compounds).

The BTEX compounds may be extracted from the sample using a solid phase microextractor to which the BTEX compounds absorb, for example, using preparative capillary gas chromatography (PCGC) with a silica open column and pentane solvent. The isotopocule composition of the BTEX compounds may then be measured using high-resolution mass spectrometry or other suitable spectroscopic methods like high-precision/resolution optical spectroscopy, for example, tunable laser infrared spectroscopy. Generally, for such methods, about 20 micromoles to about 50 micromoles (preferably about 40 micromoles) of BTEX compounds are needed to perform such methods.

The isotopocule composition of the BTEX compounds are then used to identify one or more characteristics of the sample from which the BTEX compounds were isolated. Examples of characteristics include, but are not limited to, the source of the sample, a condition at which the sample formed or was last equilibrated, migration time from source to sample location, weathering of the sample, degree to which the sample is anthropogenic or naturally-occurring, and the like, and any combination thereof.

For identifying the source of the sample, the isotopocule composition of the BTEX compounds of the sample can then be compared to a database (e.g., on a computer) of isotopocule composition of the BTEX compounds of a variety of sources and/or the isotopocule composition of the BTEX compounds of a suspected source.

For identifying a condition at which the sample formed or was last equilibrated, a series of standard, artificial fluids can be prepared where an initial hydrocarbon fluid is exposed to a catalyst at a temperature. The reaction is performed for a sufficient time to drive the isotopocule composition of the BTEX compounds in the hydrocarbon fluid to or toward thermodynamic equilibrium. The series of standard fluids can be prepared with different hydrocarbon fluids and/or at different temperatures. At different temperatures, certain isotopocules will be preferentially concentrated relative to other isotopocules. Standard fluids prepared at different temperatures may then be used to generate instrument calibrations, which, in turn, allow for determination of isotopocule temperatures at which unknown sample fluids were apparently equilibrated.

Identifying a condition at which the sample formed or was last equilibrated may also be useful in narrowing the potential sources and/or identifying the source of the sample.

For migration time from source to sample location, rates and isotopocule patterns associated with natural alteration can be estimated via laboratory experiments conducted under analogous conditions.

For chemical weathering of the sample, the BTEX compounds may undergo reactions that add substituents to the compound. For example, photo-oxidation may add a —OH group to the ring of the BTEX compounds. In this instance, the location and abundance of $^{13}C$ in the ring is not altered. Therefore, the $^{13}C$ portion of the isotopocule composition can be used for identifying and/or narrowing a source, and the change in the amount of —OH derivatized BTEX compounds can be used to estimate the amount of weathering of the sample.

For biological weathering, certain positions on the BTEX compounds may be preferentially attacked by petroleum-degrading organisms. In this instance, the location and abundance of $^{13}C$-$^{13}C$ bonds may be sensitive to the degree of degradation. Therefore, the position-specific $^{13}C$-$^{13}C$ isotopocule composition could be used to estimate the change in environmental concentration due to biological removal.

As described above, the conditions under which a hydrocarbon is formed (or last equilibrated) can change the isotopocule composition of said hydrocarbon. Further, the abundance of carbon isotopes $^{13}C$ and hydrogen isotopes $^{2}H$ in the starting material to form said hydrocarbon will also affect the isotopocule composition. Naturally-occurring hydrocarbons (e.g., petroleum) are generated in subsurface sediments from previously-living organic matter and often have different relative abundances of carbon isotopes $^{13}C$ and hydrogen isotopes $^{2}H$ depending on the depth, temperature, and pressure at which the hydrocarbon was generated, the character of the sedimentary organic matter, and/or the geographic location. Taking into account these factors, the degree to which the sample, from which BTEX compounds are extracted, is anthropogenic and naturally-occurring can be determined.

Hydrocarbon fluids in the environment may be mixtures of two or more fluids from separate, unrelated sources. Compositions of fluids determined by the above methods may be used to differentiate mixed fluids into their differently-sourced components. The differentiation (or deconvolution) may be done via inverse numerical methods and/or via minimization of errors in observed data compared to results simulated by forward modeling methods. Such methods may include Monte Carlo simulations, least-squares minimization methods, and other numerical algorithms.

The methods described herein can combine the isotopocule composition analysis with other hydrocarbon fingerprinting analyses to determine a characteristic of the sample from which the BTEX compounds are isolated. Examples of other hydrocarbon fingerprinting analyses include, but are not limited to, the distribution and/or ratio of specific hydrocarbons (e.g., n-alkanes, polycyclic aromatic hydrocarbons, and the like), the ratio of carbon isotopes, the absence/presence of markers (e.g., biomarkers), and the like, and any combination thereof. Analysis methods may include, but are not limited to, gas chromatography, liquid chromatography, nuclear magnetic resonance spectroscopy, infrared spectroscopy, Raman spectrometry, and the like, and any combination thereof.

The methods described herein can, and in many embodiments must, be performed using computing devices or processor-based devices. "Computer-readable medium" or "non-transitory, computer-readable medium," as used herein, refers to any non-transitory storage and/or transmission medium that participates in providing instructions to a processor for execution. Such a medium may include, but is not limited to, non-volatile media and volatile media. Non-volatile media includes, for example, NVRAM, or magnetic or optical disks. Volatile media includes dynamic memory, such as main memory. Common forms of computer-readable media include, for example, a floppy disk, a flexible disk, a hard disk, an array of hard disks, a magnetic tape, or any other magnetic medium, magneto-optical medium, a CD-ROM, a holographic medium, any other optical medium, a RAM, a PROM, and EPROM, a FLASH-EPROM, a solid-state medium like a memory card, any other memory chip or cartridge, or any other tangible medium from which a computer can read data or instructions. When the computer-readable media is configured as a database, it is to be understood that the database may be any type of database, such as relational, hierarchical, object-oriented, and/or the like. Accordingly, the embodiments of the present systems and methods may be considered to include a tangible storage medium or tangible distribution medium and prior art-recognized equivalents and successor media, in which the software implementations embodying the present techniques are stored.

The methods described herein may be performed using computing devices or processor-based devices that include a processor; a non-transitory, computer-readable medium coupled to the processor; and instructions provided to the non-transitory, computer-readable medium, wherein the instructions are executable by the processor to perform the methods described herein (such as computing or processor-based devices that may be referred to generally by the shorthand "computer"). For example, a system may comprise: a processor; a non-transitory, computer-readable medium coupled to the processor; and instructions provided to the non-transitory, computer-readable medium, wherein the instructions are executable by the processor to perform a method comprising: comparing an isotopocule composition of BTEX compounds extracted from a sample to a database of isotopocule compositions of BTEX compounds from different sources and/or having been exposed to different conditions; and identifying a characteristic of the sample based on the comparison.

Example Embodiments

A first nonlimiting example embodiment of the present disclosure is a method comprising: extracting BTEX compounds from a sample; measuring the isotopocule composition of the BTEX compounds; and determining a characteristic of the sample based on the isotopocule composition. The first nonlimiting example embodiment may further include one or more of: Element 1: wherein the sample comprises water, petroleum, petrochemicals, and/or solid material; Element 2: wherein the extracting of the BTEX compounds uses preparative capillary gas chromatography; Element 3: wherein the measuring of the isotopocule composition uses high-resolution mass spectrometry; Element 4: wherein the measuring of the isotopocule composition uses tunable laser infrared spectroscopy; Element 5: wherein the characteristic of the sample comprises one or more selected from the group consisting of: a source of the sample, a condition at which the sample formed or was last equilibrated, a migration time from a source to a sample location, weathering of the sample, and degree to which the sample is anthropogenic and naturally-occurring; Element 6: Element 5 and wherein the source is a plurality of sources; Element 7: Element 6 and wherein the characteristic of the sample further comprise differentiation of the plurality of sources; Element 8: Element 7 and wherein the differentiation comprise (a) inverse numerical methods and/or (b) minimization of errors in observed data compared to results simulated by forward modeling methods; Element 9: the method further comprising: hydrocarbon fingerprinting the sample, wherein the hydrocarbon fingerprinting is selected from the group consisting of: a distribution of specific hydrocarbons in the sample, a ratio of specific hydrocarbons in the sample, a ratio of carbon isotopes in the sample, an absence or presence of biomarkers in the sample, and any combination thereof; Element 10: Element 9 and wherein the hydrocarbon fingerprinting involves one selected from the group consisting of: gas chromatography, liquid chromatography, nuclear magnetic resonance spectroscopy, infrared spectroscopy, Raman spectrometry, and any combination thereof. Examples of combinations include, but are not limited to, Element 1 in combination with one or more of Elements 2-10; Element 2 in combination with one or more of Elements 3-10; and Element 3 in combination with one or more of Elements 4-10; Element 5 (optionally in combination with one or more of Elements 6-8) in combination with one or more of Elements 9-10.

A second nonlimiting example embodiment of the present disclosure is a method comprising: extracting BTEX compounds according to Compound 1 from a sample; measuring the isotopocule composition of the BTEX compounds; and determining a characteristic of the sample based on the isotopocule composition, wherein the characteristic of the sample comprises one or more selected from the group consisting of: a source of the sample, a condition at which the sample formed or was last equilibrated, a migration time from a source to a sample location, weathering of the sample, and degree to which the sample is anthropogenic and naturally-occurring. The second nonlimiting example embodiment may further include one or more of: Element 11: wherein the sample comprises water, petroleum, petrochemicals, and/or solid material; Element 12: wherein the extracting of the BTEX compounds uses preparative capillary gas chromatography; Element 13: wherein the measuring of the isotopocule composition uses high-resolution mass spectrometry; Element 14: wherein the measuring of the isotopocule composition uses tunable laser infrared spectroscopy; Element 15: wherein the source is a plurality of sources; Element 16: Element 15 and wherein the characteristic of the sample further comprise differentiation of the plurality of sources; Element 17: Element 16 and wherein the differentiation comprise (a) inverse numerical methods and/or (b) minimization of errors in observed data compared to results simulated by forward modeling methods; Element 18: the method further comprising: hydrocarbon fingerprinting the sample, wherein the hydrocarbon fingerprinting is selected from the group consisting of: a distribution of specific hydrocarbons in the sample, a ratio of specific hydrocarbons in the sample, a ratio of carbon isotopes in the sample, an absence or presence of biomarkers in the sample, and any combination thereof; Element 19: Element 18 and wherein the hydrocarbon fingerprinting involves one selected from the group consisting of: gas chromatography, liquid chromatography, nuclear magnetic resonance spectroscopy, infrared spectroscopy, Raman spectrometry, and any combination thereof. Examples of combinations include, but are not limited to, Element 11 in combination with one or more of Elements 12-19; Element 12 in combination with one or more of Elements 13-19; and Element 13 in combination with one or more of Elements 14-19; Element 15 (optionally in combination with one or more of Elements 16-17) in combination with one or more of Elements 18-19.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the incarnations of the present inventions. At the very least, and not as an attempt to limit the application of the doctrine of equivalents to the scope of the claim, each numerical parameter should at least be construed in light of the number of reported significant digits and by applying ordinary rounding techniques.

One or more illustrative incarnations incorporating one or more invention elements are presented herein. Not all features of a physical implementation are described or shown in this application for the sake of clarity. It is understood that in the development of a physical embodiment incorporating one or more elements of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

Therefore, the present invention is well adapted to attain the ends and advantages mentioned as well as those that are inherent therein. The particular examples and configurations disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative examples disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:
1. A method comprising:
   extracting BTEX compounds from a sample;
   measuring an isotopocule composition of the BTEX compounds; and
   determining a characteristic of the sample based on the measured isotopocule composition,
   wherein the characteristic of the sample comprises a weathering of the sample,
   wherein the weathering of the sample is a chemical weathering of the sample or a biological weathering of the sample,
   wherein an amount of the chemical weathering is estimated based on an identified change in an amount of hydroxide (—OH) in the sample, or
   wherein an amount of the biological weathering is estimated based on an identified change in location and quantity $^{13}C$-$^{13}C$ of bonds in the sample.
2. The method of claim 1, wherein the sample comprises water, petroleum, petrochemicals, and/or solid material.
3. The method of claim 1, wherein the extracting of the BTEX compounds uses preparative capillary gas chromatography.
4. The method of claim 1, wherein the measuring of the isotopocule composition uses high-resolution mass spectrometry.
5. The method of claim 1, wherein the measuring of the isotopocule composition uses tunable laser infrared spectroscopy.
6. The method of claim 1, wherein the characteristic of the sample further comprises a differentiation of a plurality of sources.
7. The method of claim 6, wherein the differentiation comprises (a) inverse numerical methods and/or (b) minimization of errors in observed data compared to results simulated by forward modeling methods.
8. The method of claim 1, further comprising:
   hydrocarbon fingerprinting the sample, wherein the hydrocarbon fingerprinting is selected from the group consisting of: a distribution of specific hydrocarbons in the sample, a ratio of specific hydrocarbons in the sample, a ratio of carbon isotopes in the sample, an absence or presence of biomarkers in the sample, and any combination thereof.
9. The method of claim 8, wherein the hydrocarbon fingerprinting involves one selected from the group consisting of: gas chromatography, liquid chromatography, nuclear magnetic resonance spectroscopy, infrared spectroscopy, Raman spectrometry, and any combination thereof.
10. The method of claim 1, wherein the weathering of the sample is the chemical weathering of the sample.
11. The method of claim 1, wherein the weathering of the sample is the biological weathering of the sample.
12. The method of claim 1, further comprising:
   identifying a source of the sample by comparing the measured isotopocule composition with a database comprising isotopocule compositions of BTEX compounds from a variety of sources or a suspected source.

13. A method comprising:
   extracting BTEX compounds according to Compound 1 from a sample

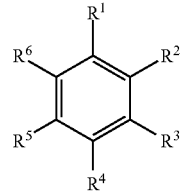

Compound 1 where R1-R6 are independently hydrogen, methyl, ethyl, n-propyl, iso-propyl, hydroxyl, carboxyl, acyl, amino, nitro, sulfo, fluoro, chloro, bromo, or iodo;
   measuring an isotopocule composition of the BTEX compounds; and
   determining a characteristic of the sample based on the measured isotopocule composition,
   wherein the characteristic of the sample comprises a weathering of the sample,
   wherein the weathering of the sample is a chemical weathering of the sample or a biological weathering of the sample,
   wherein an amount of the chemical weathering is estimated based on an identified change in an amount of hydroxide (—OH) in the sample, or
   wherein an amount of the biological weathering is estimated based on an identified change in location and quantity of $^{13}C$-$^{13}C$ bonds in the sample.
14. The method of claim 13, wherein the sample composes water, petroleum, petrochemicals, and/or solid material.
15. The method of claim 13, wherein the extracting of the BTEX compounds uses preparative capillary gas chromatography.
16. The method of claim 13, wherein the measuring of the isotopocule composition uses high-resolution mass spectrometry.
17. The method of claim 13, wherein the measuring of the isotopocule composition uses tunable laser infrared spectroscopy.
18. The method of claim 13, wherein the characteristic of the sample further comprises a differentiation of a plurality of sources.
19. The method of claim 18, wherein the differentiation comprises (a) inverse numerical methods and/or (b) minimization of errors in observed data compared to results simulated by forward modeling methods.
20. The method of claim 13, further comprising:
   hydrocarbon fingerprinting the sample, wherein the hydrocarbon fingerprinting is selected from the group consisting of: a distribution of specific hydrocarbons in the sample, a ratio of specific hydrocarbons in the sample, a ratio of carbon isotopes in the sample, an absence or presence of biomarkers in the sample, and any combination thereof.
21. The method of claim 13, wherein the weathering of the sample is the chemical weathering of the sample.
22. The method of claim 13, wherein the weathering of the sample is the biological weathering of the sample.

* * * * *